(12) United States Patent
Kadziauskas et al.

(10) Patent No.: US 7,850,680 B2
(45) Date of Patent: Dec. 14, 2010

(54) FLEXIBLE INFUSION LINE FOR OCULAR SURGERY

(75) Inventors: Kenneth E. Kadziauskas, Coto de Caza, CA (US); Tom Sutton, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 961 days.

(21) Appl. No.: 10/682,460

(22) Filed: Oct. 8, 2003

(65) Prior Publication Data
US 2005/0080375 A1  Apr. 14, 2005

(51) Int. Cl.
*A61M 1/00* (2006.01)
*A61B 18/18* (2006.01)

(52) U.S. Cl. .................. 606/6; 604/30; 604/35
(58) Field of Classification Search .......... 604/294, 604/295, 19–22, 39–42, 101.02, 103.11, 604/104; 606/6, 22, 27–31, 107
See application file for complete search history.

(56) References Cited

U.S. PATENT DOCUMENTS

| 5,084,009 | A | * | 1/1992 | Mackool | 604/22 |
| 5,476,448 | A | * | 12/1995 | Urich | 604/22 |
| 5,554,894 | A | * | 9/1996 | Sepielli | 307/119 |
| 5,797,733 | A | * | 8/1998 | Falk et al. | 417/416 |
| 6,106,494 | A | * | 8/2000 | Saravia et al. | 604/35 |
| 6,589,201 | B1 | * | 7/2003 | Sussman et al. | 604/27 |
| 6,979,328 | B2 | * | 12/2005 | Baerveldt et al. | 606/41 |
| 2004/0229814 | A1 | * | 11/2004 | Dillon | 514/18 |

OTHER PUBLICATIONS

English translation of JP 2000-120602 A to Rehn et al.*

* cited by examiner

*Primary Examiner*—Melanie J Hand

(57) ABSTRACT

An infusion source provides for a fluid supply and an irrigation line interconnecting the fluid supply with an irrigation lumen of an ocular handpiece. An accumulator is disposed in fluid communication with irrigation line and the irrigation lumen includes an expandable wall for enabling accumulation of fluid within the tubular member during occlusion of the aspiration lumen, and enhanced flow of the fluid of the irrigation lumen upon clearing of the occlusion.

31 Claims, 4 Drawing Sheets

FLEXIBLE INFUSION LINE FOR OCULAR SURGERY

The present invention generally relates to ocular surgery and is more particularly directed to an infusion source for providing irrigation fluid to a surgical site. More specifically, the present invention may be directed to irrigation tubing systems utilized with handpieces for the removal of cataracts.

As a specific example of ocular surgery the removal of cataracts through phacoemulsification utilizes a vibrated needle for fracturing cataractic tissue and subsequent aspiration of fragmented tissue through a phacoemulsification needle or separate aspiration lumen.

In phacoemulsification procedures a handpiece is provided for vibrating a needle, typically at ultrasonic frequencies, which is utilized to break up the crystalline lens of an eye into minute fragments. The needle typically includes a sleeve and an irrigation fluid lumen is established around the needle for supplying irrigation fluid to the surgical site, although separate irrigation and aspiration needles may be used.

The irrigation fluid is utilized to flush the fragmented particles from the eye and, importantly, controlled to maintain interocular pressure during surgery.

During the procedure, an occlusion of the aspiration lumen may occur when a fragmented tissue piece is aspirated to the aspiration lumen and does not freely pass therethrough.

When such an occlusion occurs, a negative pressure in the aspiration lumen between the surgical site and a vacuum pump increases. If the occlusion is suddenly removed, either by continued vibration of the needle or increased suction, there is a tendency for the fluid within the surgical site to rush suddenly into the aspiration lumen. This can cause undesirable pressure variation in the eye.

The present invention is directed to an infusion source, which enhances irrigation fluids to an ocular site with insured regulation of pressure within the eye during surgery.

SUMMARY OF THE INVENTION

An infusion source in accordance with the present invention may include a phacoemulsification handpiece having a needle with an irrigation lumen and an aspiration lumen.

Alternatively, a separate irrigation handpiece with an irrigation lumen and aspiration handpiece with an aspiration lumen may be utilized. A fluid supply is interconnected with the irrigation lumen by an irrigation line and a tubular member may be disposed in irrigation fluid communication with the irrigation line and the irrigation lumen. The tubular member may be disposed in parallel with the irrigation lumen or in series therewith.

The tubular member includes an expandable wall for enabling accumulation of fluid within the tubular member during occlusion of the aspiration lumen and enhanced flow of fluid into the irrigation upon clearing of the occlusion.

Accordingly, the tubular member functions to store energy, which is then utilized, to increase or enhance fluid flow following the clearing of the occlusion.

Preferably, the tubular member is disposed proximate the handpiece and the tubular walls are formed from elastic material. This elasticity enables the tubular member to shrink to a diameter smaller than a nominal diameter, thereby allowing for greater volume of infusion then is possible with the irrigation line itself.

In one embodiment of the present invention, the tubular member may include a sheath disposed around the expandable wall. This sheath may be rigid or flexible and take the form of a mesh.

Alternatively, in another embodiment of the present invention, the sheath and the expandable wall are integrally molded. In this embodiment, a plurality of expandable walls may be molded in a spaced apart relationship within the sheath. In this instance, the expandable walls being formed of an elastic material are relatively thin compared with the thickness of the sheath.

In an alternative embodiment of the present invention, an infusion source for a phacoemulsification handpiece having a needle, an irrigation lumen, and an aspiration lumen, generally includes a fluid supply and an irrigation line interconnecting the fluid supply and the irrigation lumen.

An accumulator is provided and disposed in fluid communication with the irrigation line and irrigation lumen with the accumulator including a housing and an expandable bladder therein for enabling accumulation of fluid during occlusion of the aspiration lumen and enhanced flow of fluid into the irrigation lumen upon clearing of the occlusion.

In this embodiment, a pneumatic access is provided to the housing for controlling expansion and contraction of the bladder. In that regard, a control system may be provided for monitoring the aspiration lumen occlusion and controlling the pneumatic pressure within the housing in order to control the bladder expansion and contraction. In this embodiment, the bladder may include accordion pleated walls and the housing may be tubular.

BRIEF DESCRIPTION OF THE DRAWINGS

The advantages and features of the present invention will be better understood by the following description when considered in conjunction with the accompanying drawings of which.

DETAILED DESCRIPTION

Figure 1:
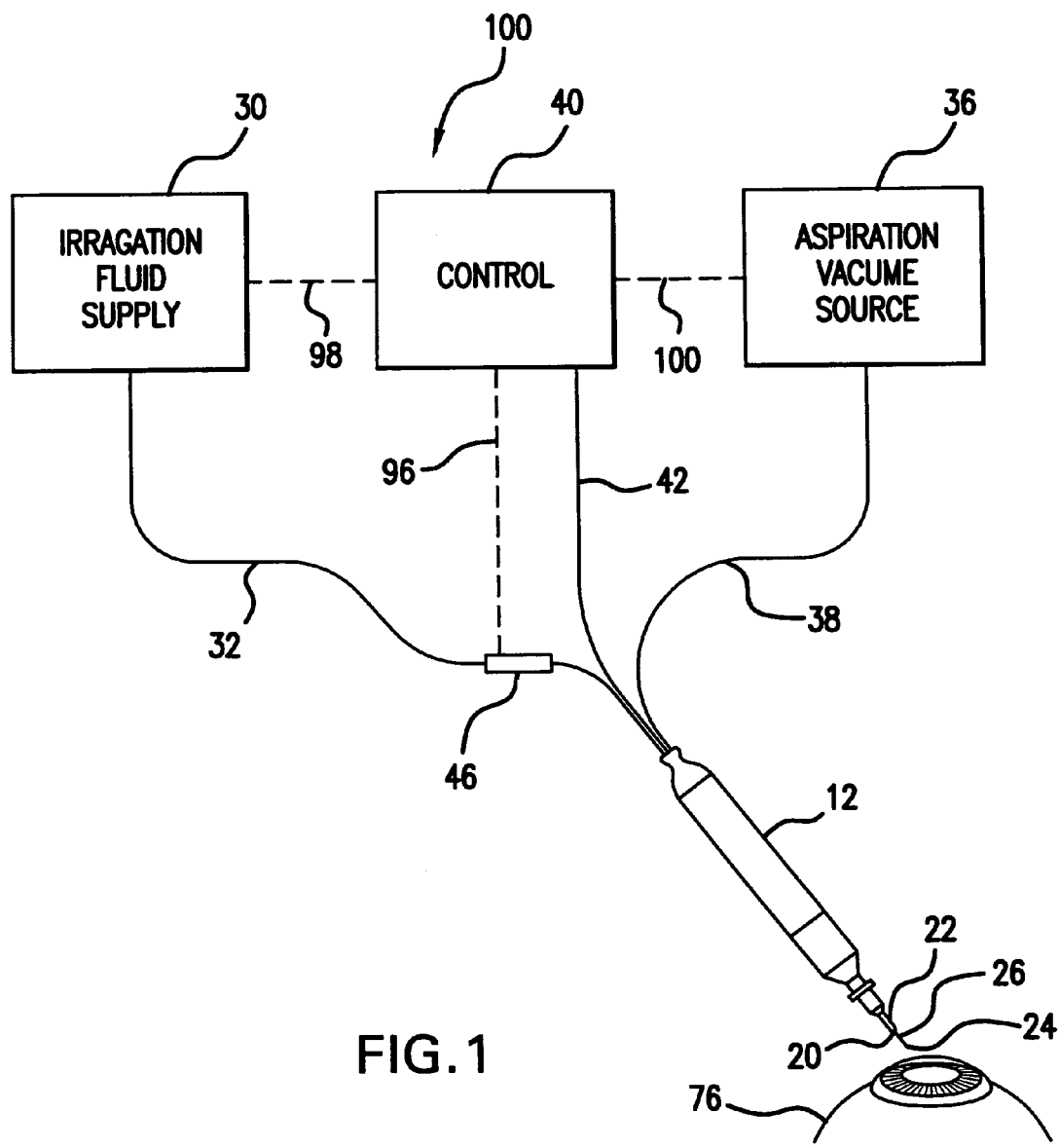
FIG. 1 is a representation of an infusion source and handpiece generally showing an irrigation fluid supply, control, aspiration and vacuum source, an accumulator, or tubular member, disposed within an irrigation line interconnecting the fluid supply with an irrigation lumen in a phacoemulsification needle controlled by the handpiece.

With reference to FIG. 1, one embodiment to the present invention encompasses an infusion source 10 for a phacoemulsification handpiece 12 having a needle 16 with an irrigation lumen 20 established by a sleeve 22 around the needle 16 and an aspiration lumen 24 through the needle 16. The handpiece 12 and needle 16, along with sleeve 22, may be of any conventional design.

More particularly, the infusion source 10 includes an irrigation fluid supply 30, along with an irrigation line 32, interconnecting the fluid supply 30 and the irrigation lumen 20. The supply 30 may be of any conventional design and include an elevated vessel and/or a fluid pump. An aspiration vacuum source 36, of any suitable design, is interconnected with the aspiration lumen 24 by an aspiration line 38 and control of the handpiece 12 is driven by a controller 40 through a power line 42.

An accumulator, or tubular member, 46 is disposed in fluid communication with the irrigation line 32 and irrigation lumen 20, for enabling accumulation of fluid within the tubular member 46 during occlusion of the aspiration lumen 24 and enhanced flow of fluid into the irrigation lumen 20 upon clearing of the occlusion as will be hereinafter described in greater detail.

Figure 2:
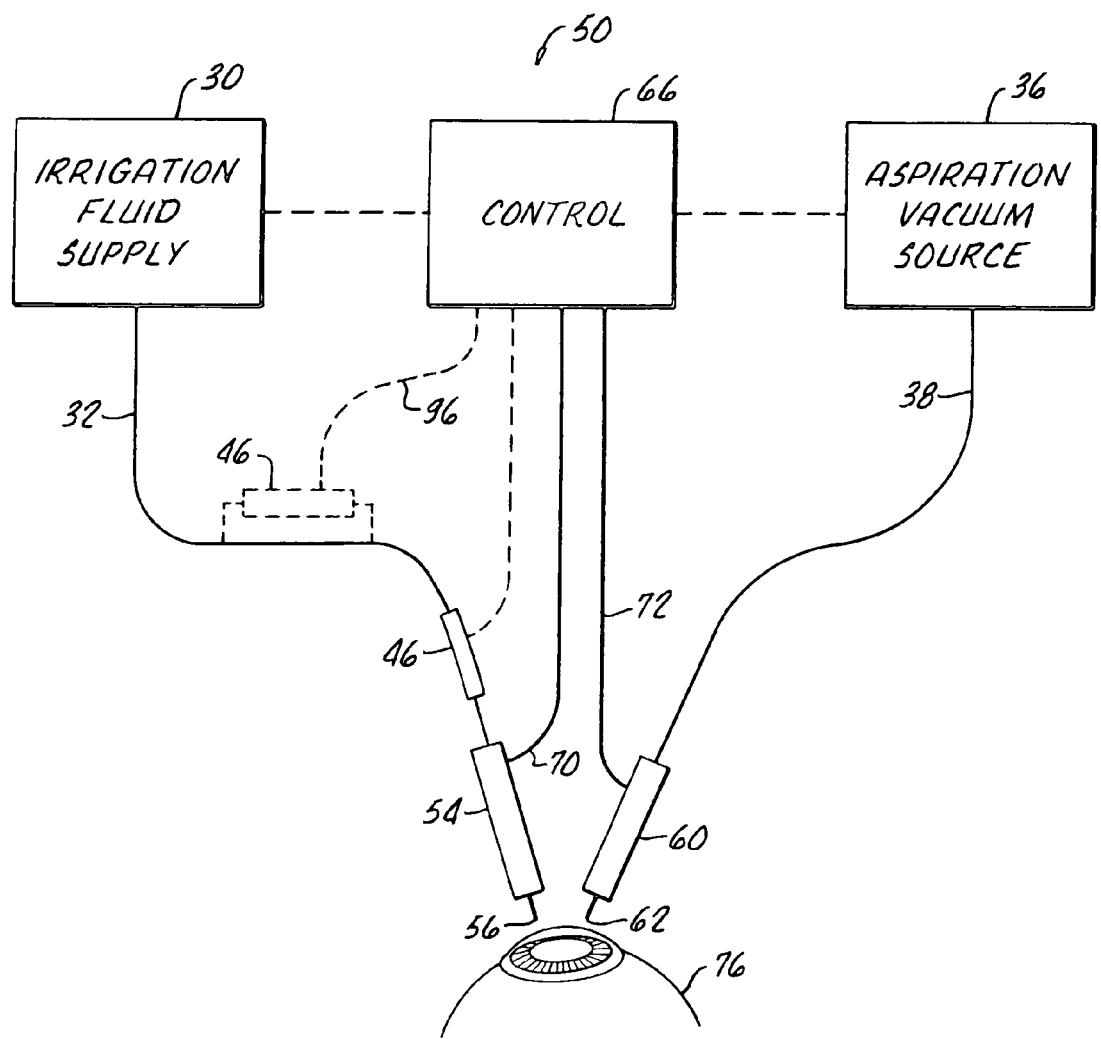
FIG. 2 is a representation of an infusion source for use with separate irrigation and aspiration lumens.

An alternative embodiment 50 of the present invention is illustrated in FIG. 2 with common character references indicating identical or substantially similar components as hereinabove described in connection with the embodiment 10, FIG. 1.

An infusion source 50 is provided for use with an ocular irrigation handpiece 54, having an irrigation lumen 56 and an ocular aspiration handpiece 60, including an aspiration lumen 62. A controller 66 coordinates operation of the handpieces 54, 60 through lines 70 and 72.

Other instruments, not shown, may be utilized in performing ocular surgery on an eye 76.

Referring to both FIG. 1 and FIG. 2, the accumulator, or tubular member 46, is preferably disposed proximate the handpieces 12 and 54, although it may he disposed at any position along the line 32. Further, as shown in solid line in FIGS. 1 and 2, the tubular member 46 may be disposed in serial fluid communication with the irrigation line 32 and irrigation lumens 20 and 56. Or, as illustrated in dashed line, the accumulator, or tubular member, 46 may be disposed in a parallel fluid relationship with the irrigation line 32. In an embodiment, tubular member 46 comprises an input port and an output port. In an embodiment, where tubular member 46 is disposed in parallel fluid relationship with irrigation line 32, the input port and output port are coupled to the irrigation line as illustrated in FIG. 2.

Figure 3:
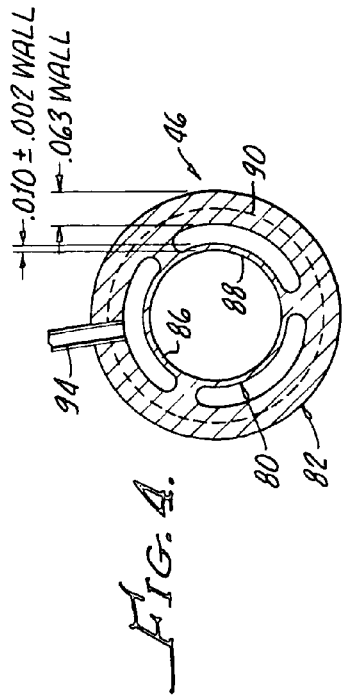
FIG. 3 is an enlarged perspective view of the accumulator, or tubular member, shown in FIG. 1 in partial cross section illustrating expandable walls for enabling accumulation of fluid.
Figure 4:
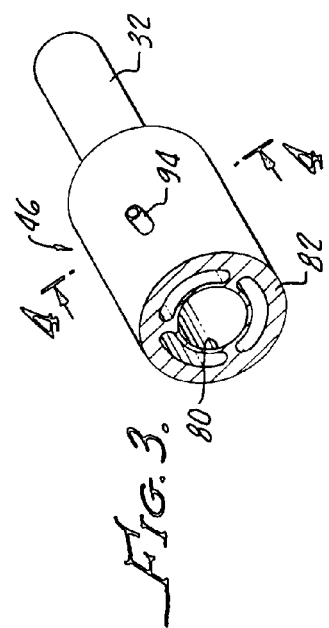
FIG. 4 is an enlarged cross sectional view of the member shown in FIG. 3.

With reference to FIGS. 3 and 4, the tubular member 46 is illustrated in cross-sectional format showing an expandable wall 80 with a sheath 82 disposed therearound. Preferably, the tubular member walls are formed from elastic materials such as, for example, silicone, and the sheath 82 is also flexible, and, preferably, the sheath 82 and expandable walls 80 are integrally molded. Additional expandable walls, 86 and 88 may be provided in a spaced apart relationship within the sheath 82.

For purposes of illustration, the tubular member 46 may have a length of approximately 12" with an inner wall diameter of approximately 0.25" and a sheath inside diameter of approximately of 0.35". The expandable walls 86 may have a thickness of about 0.010" and the sheath may have a thickness of about 0.063".

Preferably, the sheath 82 is flexible, however, a rigid sheath may be provided or the sheath 82 strengthened by use of an embedded mesh 90 illustrated in dashed line in FIG. 4.

As shown in both FIGS. 3 and 4, a pneumatic access 94 may be provided to control expansion and extraction of the expandable walls 80, 86, and 88 through a line 96 connected to the controller 40. The controller 40 may further be connected to the irrigation fluid supply 30 and aspiration vacuum source 36 by lines 98-100 to coordinate the operation of accumulator 46.

Figure 5:
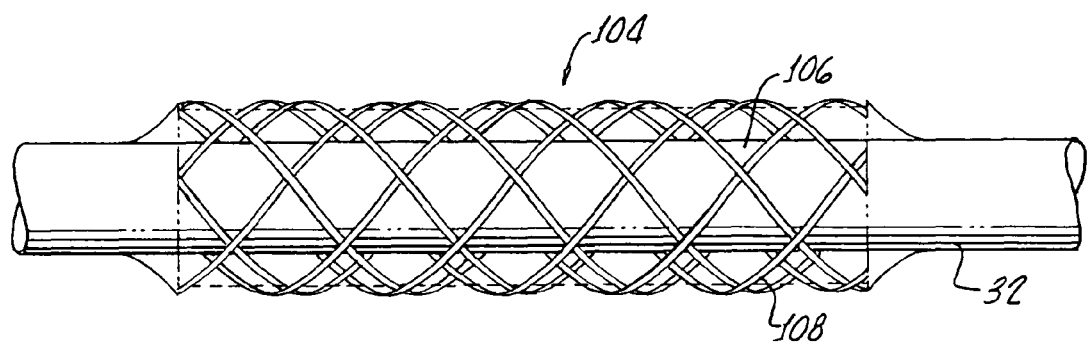
FIG. 5 is a side view of another embodiment of the present invention, which includes a tubular member having expandable walls with a mesh sheath therearound.

An alternative accumulator embodiment 104 is illustrated in FIG. 5, which includes a balloon type section 106 surrounded by a flexible spaced apart mesh 108 to prevent overexpansion of section 106.

Figure 6:
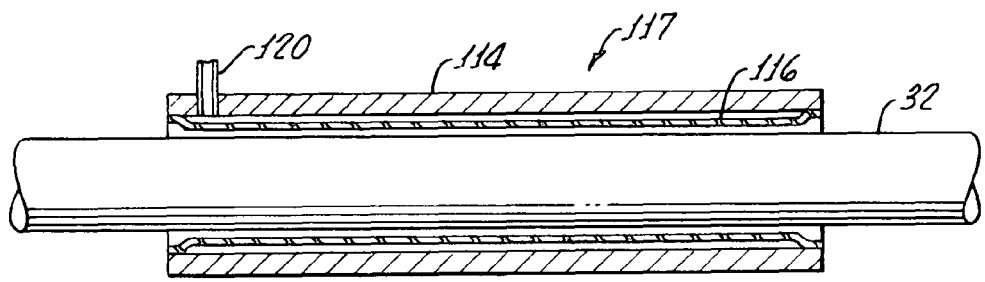
FIG. 6 illustrates yet another embodiment of the present invention in cross section illustrating a bladder disposed within a housing having a pneumatic access thereto for controlling expansion and contraction of the bladder.

Still another accumulator embodiment 112 is illustrated in FIG. 6, which includes a tubular housing 114 for containing an expandable bladder 116, which enables accumulation of fluid during occlusion of the aspiration lumen 24 and enhanced flow of fluid into the irrigation lumen 20 on clearing of the occlusion.

As hereinabove described, a pneumatic access 120 is provided, which, in combination with the controller 140, enables monitoring of aspiration lumen 24 occlusion and controlling pneumatic pressure within the housing 114 in order to control bladder 116 expansion and contraction.

Figure 7:
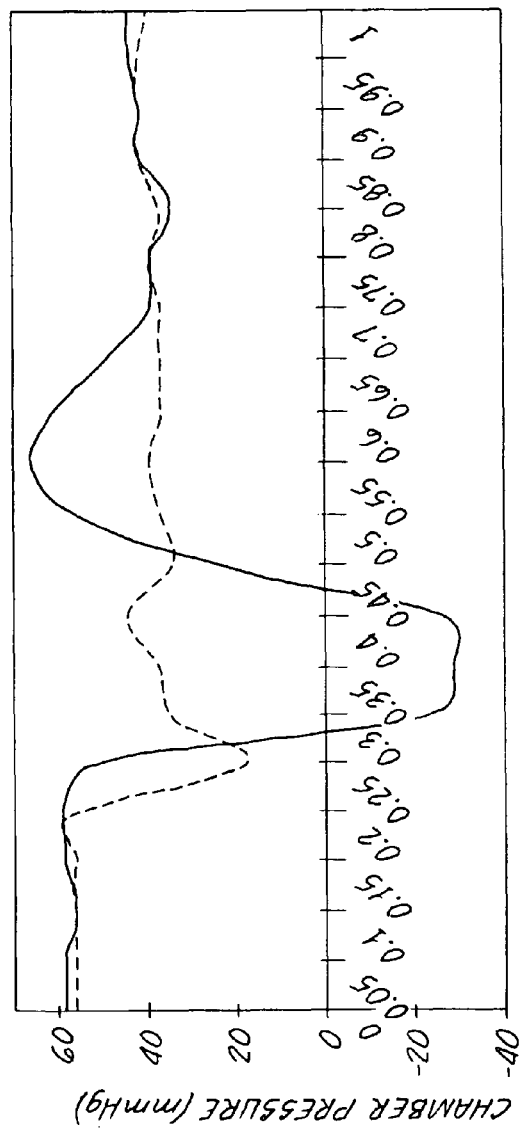
FIG. 7 is a plot showing pressure variation as a function of aspiration lumen occlusion for a convention irrigation line without the accumulator in accordance with the present invention and the pressure variation with the accumulator in accordance with the present invention.

In operation, the accumulative 46 demonstrates a significant improvement to measure chamber stability in a laboratory test set-up, not shown. FIG. 7 illustrates in solid line test chamber pressure as a function of time subsequent to clearing an occlusion of aspiration lumen 24 under extreme parameters, for example, 40 cc/min aspiration flow, 500 mmHg vacuum with a 20-gauge tip. It should be appreciated that eye collapse may occur at a chamber pressure of about 10 mmHg.

Under these same conditions, the infusion source 10, incorporating the accumulator 46, provides a pressure profile as illustrated in dashed line in FIG. 7. As shown under these extreme conditions, the infusion source 10 functions to prevent collapse of the eye.

During occlusion, head pressure energy is stored in the elasticity of the expandable walls inner walls 80, 86 and 88. Following occlusion, the walls 80, 86, and 88 collapse using energy stored in the stretched walls 80, 86 and 88 to force fluid toward the handpiece 12 and through the lumen 24. In addition, the expandable and elastic walls 80, 86 and 88 are able to shrink smaller than the normal diameter, thus allowing for greater volume of fluid flow than would occur then with a relatively rigid section of tubing 32.

Although there has been hereinabove described a specific infusion source in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratedly disclosed herein suitably may be practiced in the absence of any element, which is not specifically disclosed herein. Accordingly, any and all modifications, variations, or equivalent arrangements, which may occur to those in the art, should be considered to be within the scope of the present invention as defined in the appended claims.

What is claimed is:

1. An infusion source for a ocular surgery comprising:
a fluid supply;
an irrigation line interconnecting said fluid supply and an irrigation lumen; and
a tubular member separate from, and in a parallel fluid relationship with, said irrigation line, said tubular member comprising an input port and an output port, wherein the input port and the output port are coupled to the irrigation line, said tubular member having an expandable wall configured to expand during occlusion of an aspiration lumen.

2. The infusion source according to claim 1, wherein said tubular member is disposed proximate a handpiece effective for use in a phacoemulsification procedure.

3. The infusion source according to claim 1, wherein the tubular member wall is formed from an elastic material.

4. The infusion source according to claim 1, wherein the tubular member comprises a sheath disposed around the expandable wall.

5. The infusion source according to claim 4, wherein said sheath is rigid.

6. The infusion source according to claim 4, wherein said sheath is flexible.

7. The infusion source according to claim 6, wherein said sheath is a mesh.

8. The infusion source according to claim 6, wherein said sheath and expandable wall are integrally molded.

9. The infusion source according to claim 8, further comprising a plurality of expandable walls molded in a spaced apart relation within said sheath.

10. The infusion source according to claim 9, wherein said expandable walls and said sheath are formed from an elastic material, said expandable walls being relatively thin compared with the thickness of the sheath.

11. The infusion source according to claim 10, wherein said sheath is a mesh.

12. The infusion source according to claim 1, further comprising a pneumatic access to said expandable wall for controlling expansion and contraction of said expandable wall.

13. The infusion source according to claim 1, further comprising a handpiece having a needle with said irrigation lumen.

14. An infusion source for a ocular surgery comprising:
a fluid supply;
a handpiece including an irrigation lumen;
an irrigation line interconnecting said fluid supply and the irrigation lumen;
an elongate tubular member disposed in fluid communication with said irrigation line, said tubular member having an expandable wall configured to expand during occlusion of an aspiration lumen, the tubular member comprising a sheath disposed around the expandable wall; and
a plurality of expandable walls molded in a spaced apart relation within said sheath;
wherein said sheath is flexible; and
wherein said sheath and expandable wall are integrally molded.

15. The infusion source according to claim 14, wherein said expandable walls and said sheath are formed from an elastic material, said expandable walls being relatively thin compared with the thickness of the sheath, and the handpiece is effective for use during a phacoemulsification procedure.

16. An ocular surgical system for performing ocular surgery on an eye, comprising:
a handpiece driven by a controller through a power line;
an irrigation lumen;
a fluid supply;
an irrigation line interconnecting said fluid supply and said irrigation lumen; and
a tubular member separate from, and in a parallel fluid relationship with, said irrigation line, said tubular member comprising an input port for receiving fluid from said irrigation line, said tubular member further comprising an output port, wherein the input port and the output port are coupled to the irrigation line, said tubular member having an expandable wall configured to expand during occlusion of an aspiration lumen.

17. The ocular surgical system according to claim 16, wherein said tubular member is disposed proximate the handpiece.

18. The ocular surgical system according to claim 16, wherein the tubular member wall is formed from an elastic material.

19. The ocular surgical system according to claim 16, wherein the tubular member comprises a sheath disposed around the expandable wall.

20. The ocular surgical system according to claim 19, wherein said sheath is rigid.

21. The ocular surgical system according to claim 19, wherein said sheath is flexible.

22. The ocular surgical system according to claim 21, wherein said sheath is a mesh.

23. The ocular surgical system according to claim 21, wherein said sheath and expandable wall are integrally molded.

24. The ocular surgical system according to claim 23, further comprises a plurality of expandable walls molded in a spaced apart relation within said sheath.

25. The ocular surgical system according to claim 24, wherein said expandable walls and said sheath are formed from an elastic material, said expandable walls being relatively thin compared with the thickness of the sheath.

26. The ocular surgical system according to claim 25, further comprising a pneumatic access to said expandable wall for controlling expansion and contraction of said expandable wall.

27. An infusion source for a ocular surgery comprising:
a fluid supply;
an irrigation line interconnecting said fluid supply and an irrigation lumen; and
a tubular member separate from, and in a parallel fluid relationship with, said irrigation line, said tubular member in fluid communication with said irrigation line and said irrigation lumen, said tubular member having an expandable wall configured to expand during occlusion of an aspiration lumen;
wherein the tubular member comprises a flexible sheath disposed around the expandable wall, said sheath and expandable wall being integrally molded.

28. An ocular surgical system for performing ocular surgery on an eye, comprising:
a handpiece driven by a controller through a power line;
an irrigation lumen;
a fluid supply;
an irrigation line interconnecting said fluid supply and said irrigation lumen; and
a tubular member separate from, and in a parallel fluid relationship with, said irrigation line, said tubular member in fluid communication with said irrigation line and said irrigation lumen, said tubular member having an expandable wall configured to expand during occlusion of an aspiration lumen;
wherein the tubular member comprises a flexible sheath disposed around the expandable wall, said sheath and expandable wall being integrally molded.

29. The infusion source according to claim 1, wherein said tubular member comprises an output port in fluid communication with said irrigation line.

30. The ocular surgical system according to claim 16, wherein said tubular member comprises an output port in fluid communication with said irrigation line.

31. An ocular surgical system for performing ocular surgery on an eye, comprising:
a fluid supply;

a handpiece configured to receive fluid from said fluid supply;

an irrigation line interconnecting said fluid supply and said handpiece;

a tubular member connected to said irrigation line, said tubular member having an expandable wall configured to expand during occlusion of an aspiration lumen, said irrigation line including a segment in parallel fluid relationship with said tubular member;

a first fluid path from said fluid supply to said handpiece, said first fluid path including said tubular member, said first fluid path bypassing said segment of said irrigation line; and a second fluid path from said fluid supply to said handpiece, said second fluid path including said segment of said irrigation line, said second fluid path bypassing said tubular member.

* * * * *